United States Patent [19]

Fukui

[11] Patent Number: 4,849,180
[45] Date of Patent: Jul. 18, 1989

[54] ALCOHOL SELECTIVE GAS SENSOR

[75] Inventor: Kiyoshi Fukui, Osaka, Japan

[73] Assignee: New Cosmos Electric Co., Ltd., Osaka, Japan

[21] Appl. No.: 106,933

[22] Filed: Oct. 5, 1987

Related U.S. Application Data

[63] Continuation of Ser. No. 827,038, Feb. 7, 1986, abandoned.

[30] Foreign Application Priority Data

Feb. 12, 1985 [JP] Japan .................... 60-23541

[51] Int. Cl.$^4$ ............................. G01M 27/04
[52] U.S. Cl. ........................... 422/98; 338/34;
422/84; 422/94; 436/131; 436/132
[58] Field of Search ................ 422/84, 84, 98;
436/131, 139, 132; 338/34

[56] References Cited

U.S. PATENT DOCUMENTS 3,865,550 2/1975 Bott et al. ................ 436/151
3,953,173 4/1976 Obayashi et al. .......... 422/83
4,015,230 3/1977 Nitta et al. ............... 422/98
4,242,303 12/1980 Takahashi et al. ......... 436/132
4,453,151 6/1984 Leary et al. .............. 422/98

FOREIGN PATENT DOCUMENTS 57-118151 7/1982 Japan .
0168949 5/1983 Japan .................... 436/131
0189546 5/1983 Japan .................... 436/132

Primary Examiner—Barry S. Richman
Assistant Examiner—Timothy M. McMahon
Attorney, Agent, or Firm—Jones, Tullar & Cooper

[57] ABSTRACT

An alcohol selective gas sensor including a detecting electrode and a semiconductor detecting element in contact with the detecting electrode, the semiconductor detecting element comprising tin oxide ($SnO_2$) and a metal oxide of at least one of alkaline earth metals (Be, Mg, Ca, Sr, Ba) carried by the tin oxide, the metal oxide being contained in an amount of about 0.5 mol % or above.

5 Claims, 3 Drawing Sheets

ALCOHOL SELECTIVE GAS SENSOR

This is a continuation of co-pending application Ser. No. 827,038 field on Feb. 7, 1986, now abandoned.

BACKGROUND OF THE INVENTION

This invention relates to an alcohol selective gas sensor capable of selectively detecting alcohol gas with high sensitivity and comprising a detecting electrode and a semiconductor detecting element in contact therewith.

From the point of view of controlling air in various environments such as room air in ordinary dwelling houses, it is conceivable that various gases are present in the room air which include methane gas ($CH_4$) resulting from leakage of town gas (such as natural gas), carbon monoxide (CO) gas, hydrogen ($H_2$) gas and NOx produced by combustion, and alcohol gas due to cooking or warming of liquor. It is therefore desirable to detect alcohol such as ethanol separately from other such gases to prevent explosion of methane gas, carbon monoxide gas and hydrogen gas and poisoning by carbon monoxide gas. However, alcoholic gas tends to be detected also by a sensor intended for methane or other gas, and it is important for elimination of false alarms and malfunctioning to reduce the sensitivity of the gas sensor with respect to ethanol and other miscellaneous gases. The reduction of the sensitivity of the gas sensor per se with respect to ethanol achieved to date has not been satisfactory.

According to another method of dealing with ethanol, a sensor having no ethanol selectivity and a sensor having ethanol selectivity are combined to assure sensitivity to ethanol. An example of a known alcohol selective sensor is disclosed in Japanese patent application laid open under No. 57-118151, and this sensor comprises magnesium oxide, chromium oxide or compound oxide thereof added with silicone oxide ($SiO_2$) and/or titanium oxide ($TiO_2$) but has not been put to practical use. The reasons for being impractical may be that this sensor is the three-component type starting from the three types of raw material coarse powder and therefore, microscopically, its composition tends to lack in uniformity, and that because of the difference in presintering and calcination temperatures resistance in the air varies greatly.

Furthermore, according to a description in the above patent application, it is desirable to operate the gas sensor by waiting for about 24 hours after one measurement till a next measurement when measuring methane, ethanol and the like in order to eliminate hysteresis of the preceding measurement. This suggests that the disclosed gas sensor is slow in responding to methane, ethanol and the like, and particularly that it takes a long time from adsorption of these gases to desorption thereof by a detecting or sensing element in the sensor.

SUMMARY OF THE INVENTION

It is therefore an object of this invention to provide a gas sensor having excellent alcohol selectivity and which essentially is of the two-component type.

Another object of this invention is to provide a gas sensor having quick selectivity and response with respect to alcohol and comprising a tin oxide piece sintered or otherwise formed as a semiconductive first component and an alkaline earth metal oxide mixed with the tin oxide piece as a second component.

An alcohol selective gas sensor according to this invention has a detecting element or semiconductor element comprising tin oxide ($SnO_2$) carrying an oxide of at least one of alkaline earth metals (Be, Mg, Ca, Sr, Ba) as basic catalyst. The term "carrying" herein means a state in which, as shown in FIG. 1c of the accompanying drawings, fine particles 1 of the sintered tin oxide piece support finer particles 2 of the alkaline earth metal oxide on surfaces thereof.

According to this invention, of the alkaline earth metals those other than beryllium, namely magnesium, calcium, strontium and barium are suited for use. Preferably magnesium and calcium are used individually or in combination to constitute, together with tin oxide, the semiconductor element of an excellent alcohol selective gas sensor.

The alkaline earth metal oxide is contained in an amount of at least about 0.5 mol %, preferably about 3 mol % or more. It is sufficient if the metal oxide is contained in 25 mol % at most, as described later.

In the most preferred embodiment of this invention, calcium oxide and magnesium oxide are carried by tin oxide in an equal amount, for example 2 mol % each, to ensure reliable selectivity with respect to ethanol over a wide temperature range of 300°–600° C. as described later.

Prior to describing the embodiment, the entire aspect of this invention will be described referring to Tables 1 and 2 and FIGS. 1a–1c, 2 and 3.

The gas sensor Rs taken for example here includes a detecting electrode 3 extending through a bead-shaped detecting element 4 (FIG. 1b). An enlarged view of the detecting element 4 is as shown in FIG. 1c.

TABLE 1

| Amount of Additive: 3 mol % Sensor Temperature: 450° C. | | | |
|---|---|---|---|
| | A<br>Sensor Output<br>Variation with<br>$H_2$ (800 ppm)<br>(mV) | B<br>Sensor Output<br>Variations with<br>EtOH (800 ppm)<br>(mV) | |
| Additive | 1st Output Vol. | 2nd Output Vol. | A/B |
| NONE | 230 | 177 | 1.30 |
| MgO | 20 | 150 | 0.13 |
| CaO | 23 | 160 | 0.14 |
| SrO | 107 | 260 | 0.41 |
| BaO | 218 | 280 | 0.78 |

Table 1 shows the results obtained when the gas sensor Rs comprising the detecting element 4 formed of tin oxide carrying a 3 mol % of additive and mounted in a circuit as shown in FIG. 1a encounters a gas containing 800 ppm hydrogen and a gas containing 800 ppm ethanol at 450° C. In FIG. 1a, E denotes an electric power source, R1 and R2 denote reference resistances, R0 denotes a fixed resistance, Rs denotes the sensor, and V denotes a voltmeter. Table 1 is graphically shown in FIG. 2.

As will be clear from Table 1 and FIG. 2, where tin oxide carries no alkaline earth metal oxide, a first output voltage mV read by the voltmeter V in FIG. 1 when the gas containing 800 ppm hydrogen is encountered, divided by a second output voltage read when the gas containing 800 ppm ethanol, gives 1.30. This means that the sensitivity to hydrogen is higher than the sensitivity to ethanol.

On the other hand, where tin oxide carries a 4 mol % of magnesium oxide, calcium oxide, strontium oxide or barium oxide, the ratio of the first output voltage with respect to the second output voltage is smaller than 1.00. In the case of magnesium oxide and calcium oxide particularly, the second output voltage is 7-8 times as large as the first output voltage, which indicates that the sensitivity to ethanol is 7-8 times the sensitivity to hydrogen.

TABLE 2

| | Additive Amount Variations Sensor Temperature: 450° C. | | | | | | | | | | |
|---|---|---|---|---|---|---|---|---|---|---|---|
| mol % | 0 | 0.5 | 1 | 2 | 3 | 4 | 6 | 8 | 10 | 12 | 16 |
| MgO | 1.30 | 0.50 | 0.32 | 0.18 | 0.13 | 0.10 | 0.05 | 0.02 | 0.03 | 0.02 | 0.01 |
| CaO | 1.30 | 0.45 | 0.35 | 0.21 | 0.14 | 0.12 | 0.06 | 0.01 | 0.05 | 0.04 | 0.01 |

Table 2 shows ratios between the first and second output voltages where the mol percent of magnesium oxide and calcium oxide is varied. This table is graphically shown in FIG. 3. As will be clear from Table 2 and FIG. 3, the sensitivity to ethanol is about twice the sensitivity to hydrogen where magnesium oxide or calcium oxide is in 0.5 mol %, 7–8 times in 3 mol % and about 100 times in 16 mol %.

The sensitivity to ethanol 100 times the sensitivity to hydrogen or higher is often more than what is necessary for practical purposes. At the same time it is possible that inconveniences such as reduced durability result from excessive alkalization of tin oxide. It is therefore sufficient for magnesium oxide or calcium oxide to be carried in 25 mol % at most.

As described above, this invention provides a gas sensor comprising a detecting element formed of a tin oxide semiconductor carrying an oxide of at least one of alkaline earth metal. This construction has successfully provided alcohol selectivity for the gas sensor having as the main component tin oxide which has conventionally been the most favored semiconductor material for use in combustible gas sensors and is highly reliable. The gas sensor according to this invention has the advantages of being easy to manufacture, suitable for mass production at low cost and quick in responding to alcohol.

BRIEF DESCRIPTION OF THE DRAWINGS

The invention will be described in greater detail hereinafter with reference to the drawings, in which.

DETAILED DESCRIPTION OF THE PREFERRED EMBODIMENTS

The invention will be described further taking for example a hot wire type gas sensor R2 which employs tin oxide ($SnO_2$) as the main component of a semiconductor detecting element 4 in contact with a detector electrode 3. The meaning of "hot wire type" will be described later.

Magnesium which provides one of the representative basic catalysts was selected from alkaline earth metals. The semiconductor element 4 was impregnated with an aqueous solution of magnesium nitrate ($Mg(NO_3)_2$) at 0.48 mol/l, dried in ambient air and thereafter calcinated in the air under 600° C. for thirty minutes. As a result, the element 4 acquired alcohol sensitivity.

Figure 1A:
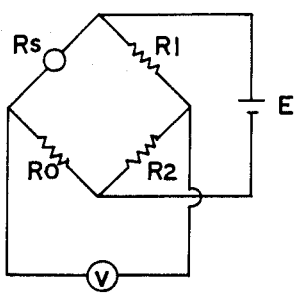
FIG. 1a is a view of a gas detecting circuit.
Figure 1B:
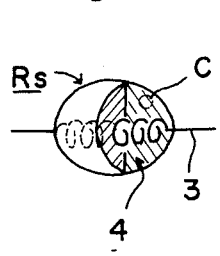
FIG. 1b is a partly broken away perspective view of a gas sensor.
Figure 1C:
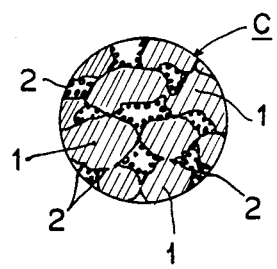
FIG. 1c is an enlarged sectional view of a portion of the sensor marked by a circle C in FIG. 1b.
Figure 2:
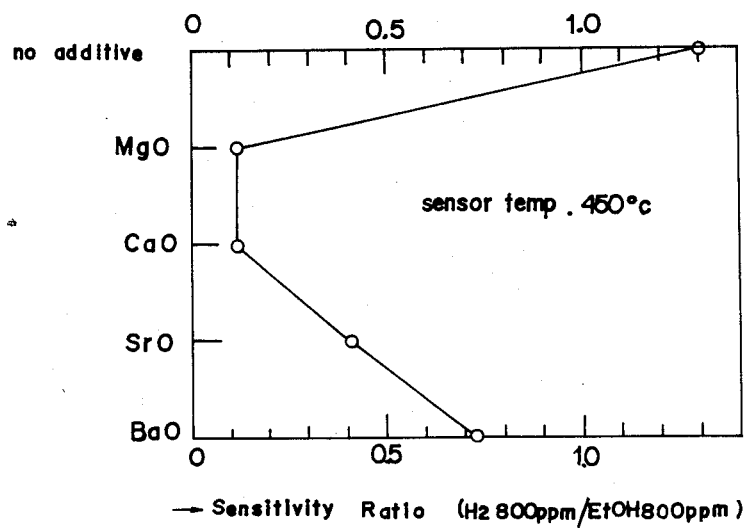
FIG. 2 is a graph showing a relationship between types of alkaline earth metal and sensitivity to ethanol.
Figure 3:
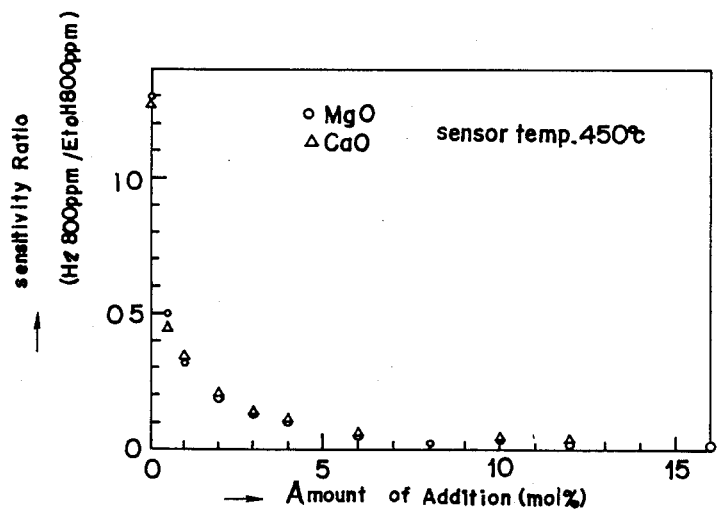
FIG. 3 is a graph showing the sensitivity to ethanol where the alkaline earth metals are added in varied amounts.

The element 4 has a fine structure as shown in FIG. 1c. As seen, ultrafine particles of magnesium oxide 2 are present on surfaces of fine particles of tin oxide. The magnesium oxide is carried by this element in an amount of about 1.6 wt. % which is about 4 mol %.

Figure 4:
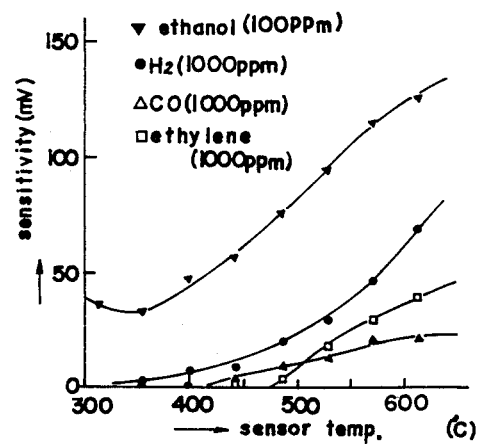
FIG. 4 is a graph showing a relationship between temperature and output voltage mV of a sensor comprising a semiconductor including magnesium oxide.
Figure 7:
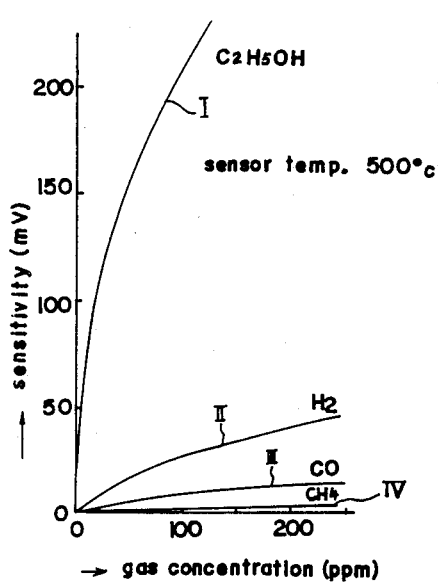
FIG. 7 is a graph showing a relationship between gas concentration and output voltage of the sensor including magnesium oxide with reference to several types of gas.

An alcohol selective gas sensor obtained as above is incorporated into one side of a known bridge circuit to provide a detecting device for selectively detecting alcoholic gas. Sensitivity of the gas sensor with respect to a gas is normally derived by measuring a difference between a bridge equilibrium potential in the air and a bridge equilibrium potential in a certain concentration of object gas (the difference being referred to hereinafter as output voltage). The results are shown in FIGS. 4 and 7. In FIG. 4, only ethanol is 100 ppm and the other gases are 1,000 ppm. Therefore, the sensitivity to ethanol is over ten times and almost twenty times the sensitivity to hydrogen or other gas regardless of temperature. FIG. 7 shows the case where the operating temperature of the gas sensor is maintained at about 500° C. Its sensitivity characteristics with respect to alcoholic gas, hydrogen gas, carbon monoxide gas and methane gas in varied concentrations are shown in curves I, II, III and IV, respectively. It will be seen that the gas sensor has a very high sensitivity to alcoholic gas compared with its sensitivity to any other gases.

Magnesium oxide is an oxide of strong basic character and easily adsorbs moisture and carbon dioxide in the atmosphere, which results in formation of magnesium carbonate and deterioration in its catalytic activity. In order to avoid this, it is necessary to set the temperature to about 300° C. or above, and preferably to 400°–500° C., to remove the adsorbed water and decompose the magnesium carbonate to the full.

This applies to the case of calcium oxide to be described later.

Influences of the sensor operating temperature are shown in FIG. 4 in relation to the cases of ethanol, hydrogen, carbon monoxide and ethylene.

Figure 9:
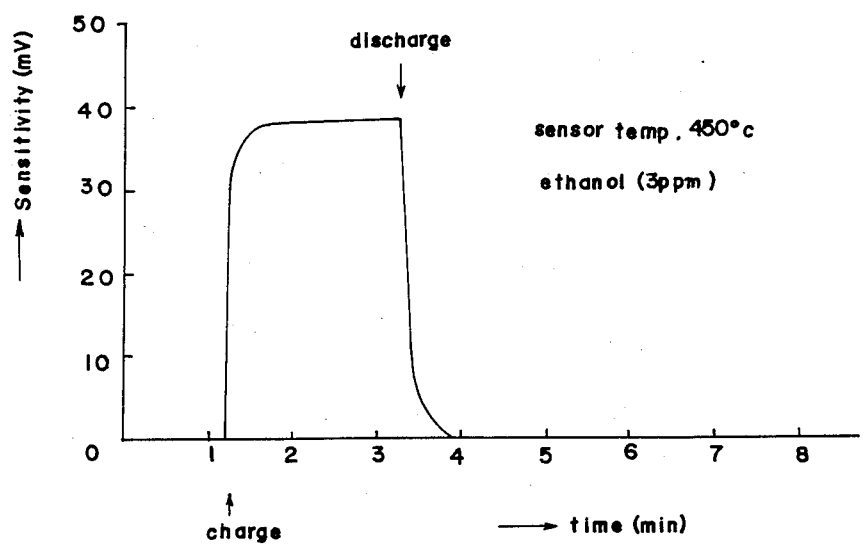
FIG. 9 is a graph showing the response of the sensor including magnesium oxide when ethanol containing gas is encountered.

FIG. 9 shows variations in the output voltage (read by a voltmeter V in FIG. 1a) occurring when the magnesium oxide containing sensor contacts a gas containing 3 ppm ethanol at a temperature of 450° C. The sensor responds within about 30 seconds when contact with the gas takes place and when the contact is eliminated.

The hot wire type gas sensor referred to hereinbefore is the type comprising a detecting electrode wire extending through or in contact with an entire length of semiconductor and acting as a heating wire.

The described embodiment is of course applicable to other types of sensors, and the semiconductor may be the sintered type or the film type.

A second embodiment will be described next.

Figure 5:
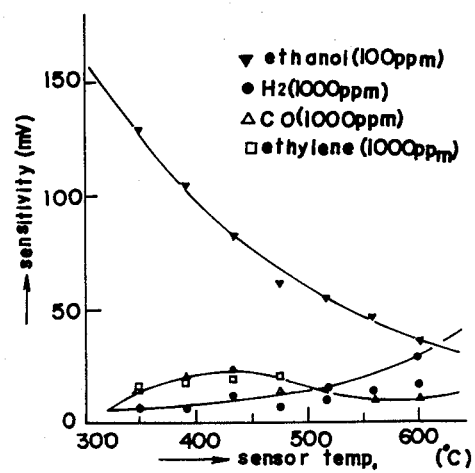
FIG. 5 is a graph showing a relationship between temperature and output voltage mV of a sensor comprising a semiconductor including calcium oxide.
Figure 8:
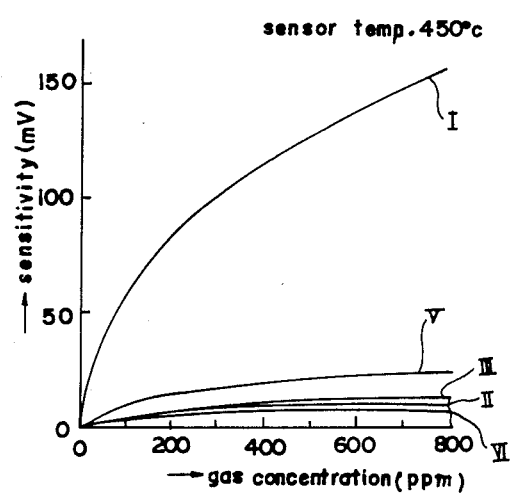
FIG. 8 is a graph similar to that of FIG. 7 and showing a relationship between gas concentration and output voltage of the sensor including calcium oxide.

A gas sensor comprising a semiconductor of sintered tin oxide containing about 4 mol % of calcium oxide is formed by employing calcium chloride ($CaCl_2$) instead of magnesium nitrate and providing the same treatments as in the first embodiment. This sensor has alcohol selectivity at 450° C. as shown in FIG. 8. Here again its sensitivity to ethanol is far greater than the sensitivity to carbon monoxide, hydrogen, ethylene and isobutane. FIGS. 5 and 8 show influences of temperature variations and concentration variations (the latter at the temperature of 450° C.), respectively. In FIG. 8, V represents isobutane and VI represents ethylene. I-III correspond to those in FIG. 7.

While output voltages of the sensor according to the first embodiment are about 50 mV at a sensor temperature of 400° C. and about 125 mV at 600° C. as shown in FIG. 4, output voltages of the sensor according to the second embodiment are about 100 mV at 400° C. and about 40 mV at 600° C. as shown in FIG. 5. That is to say the latter is directly opposite in tendency to the former in that its sensitivity to alcohol slightly decreases with a rise of temperature.

Figure 6:
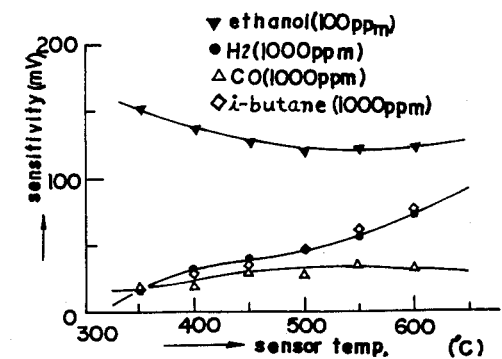
FIG. 6 is a graph similar to those of FIGS. 4 and 5 and showing a relationship between temperature and output voltage mV of a sensor comprising a semiconductor including magnesium oxide and calcium oxide.

A third embodiment is provided having regard to this fact. In this example both magnesium nitrate and calcium chloride are employed, and a presintered piece of tin oxide is immersed in an aqueous solution of the two substances to obtain a sensor comprising a tin oxide semiconductor containing 2 mol % each of magnesium oxide and calcium oxide. FIG. 6 shows a relationship between the sensitivity of this sensor and temperature variations. As seen, the sensor has a substantially constant sensitivity to ethanol or provides an output voltage of 120-130 mV in the range of 300°-600° C., particularly 400°-600° C. Since the detection voltage for hydrogen and isobutane is about 80 mV at 600° C., the sensor may seem slightly low in selectivity. However, while ethanol is 100 ppm, hydrogen and other gases are 1,000 ppm or ten times the concentration of ethanol as in the cases shown in FIGS. 4 and 5. Therefore this sensor is ten times as sensitive to ethanol as it is to hydrogen or other gases.

What is claimed is:

1. An alcohol selective gas sensor including a detecting electrode and a semiconductor detecting element in contact with the detecting electrode, said semiconductor detecting element comprising approximately 75 to 99.5 mol % of tin oxide $SnO_2$ and a metal oxide of at least one of alkaline earth metals, (Be, Mg, Ca, Sr, Ba) carried by the tin oxide, said metal oxide being contained in an amount ranging from about 0.5 to 25 mol %.

2. An alcohol selective gas sensor as defined in claim 1 wherein said metal oxide is contained in an amount exceeding about 3 mol %.

3. An alcohol selective gas sensor as defined in claim 2 wherein said metal oxide is selected from magnesium oxide and calcium oxide.

4. An alcohol selective gas sensor as defined in claim 2 wherein said metal oxide is a mixture of magnesium oxide and calcium oxide.

5. An alcohol selective gas sensor as defined in claim 4 wherein said magnesium oxide and calcium oxide are contained in a substantially equal amount.

* * * * *